United States Patent [19]

Machida

[11] Patent Number: 4,922,614
[45] Date of Patent: May 8, 1990

[54] CUTTER

[75] Inventor: Naoyoshi Machida, Seki, Japan

[73] Assignee: Kai Cutlery Center Co., Ltd., Japan

[21] Appl. No.: 188,497

[22] Filed: Apr. 29, 1988

[30] Foreign Application Priority Data

Apr. 30, 1987 [JP] Japan .............................. 62-66632[U]

[51] Int. Cl.⁵ .............................................. B26B 1/00
[52] U.S. Cl. ...................................... 30/339; 606/167
[58] Field of Search ......... 128/305; 30/40.2, 335-340, 30/329, 332

[56] References Cited

U.S. PATENT DOCUMENTS

| | | |
|---|---|---|
| 1,940,855 | 12/1933 | Friedman . |
| 2,637,904 | 5/1953 | Springer . |
| 2,650,426 | 9/1953 | Montellius . |
| 2,708,313 | 5/1955 | Steele . |
| 2,802,265 | 8/1957 | Ogden . |
| 2,960,769 | 11/1960 | Marwijcow . |
| 3,025,598 | 3/1962 | Nissen . |
| 3,085,332 | 4/1963 | Raybin . |
| 3,187,431 | 6/1965 | Mattes . |
| 3,244,317 | 4/1966 | Raybin . |
| 3,247,592 | 4/1966 | Arden . |
| 3,262,205 | 7/1966 | Scalpel . |
| 3,276,120 | 10/1966 | Scott et al. . |
| 3,412,467 | 11/1968 | Matwijcow . |
| 3,670,733 | 6/1972 | Carlisle . |
| 3,672,054 | 6/1972 | Kaufman . |
| 3,793,726 | 2/1974 | Schrank . |
| 3,832,776 | 9/1974 | Sawyer . |
| 3,905,101 | 9/1975 | Shepherd . |
| 3,906,626 | 9/1975 | Riuli . |
| 4,140,123 | 2/1979 | Curutchet . |
| 4,273,127 | 6/1981 | Auth et al. . |

FOREIGN PATENT DOCUMENTS

| | | |
|---|---|---|
| 1134793 | 8/1962 | Fed. Rep. of Germany . |
| 1144437 | 2/1963 | Fed. Rep. of Germany . |
| 102494 | 7/1917 | United Kingdom . |

Primary Examiner—Michael H. Thaler
Assistant Examiner—W. Lewis
Attorney, Agent, or Firm—Ostrolenk, Faber, Gerb & Soffen

[57] ABSTRACT

A cutter is composed of a blade body and a stem. The blade body has an engage hole made up of a grip hole and a lock hole which is narrower than the grip hole and is extended to and connected with the grip hole. A peripheral portion of the lock hole defines a marginal portion. The stem has a blade body mounting section for supporting the blade body being put thereon. The blade body mounting section includes an engage projection adapted to be fitted in the engage hole of the blade body. The engage projection has a lock groove for receiving the marginal portion. The stem is provided with a push member adapted when controlled to push a first portion, on the side of the grip hole, of the blade body, whereby in response to the pushing action of the push member a second portion, substantially facing the grip hole, of the blade body is curved and separated from the engage projection.

3 Claims, 3 Drawing Sheets

4,922,614

CUTTER

FIELD OF THE INVENTION

This invention relates to a cutter and, more particularly, to a structure for attaching and detaching a blade body which can be incorporated in blade-replaceable scalpels.

DESCRIPTION OF THE RELATED ART

A general type of blade-replaceable scalpel is disclosed in Japanese Patent Publication No. 62-7857. This scalpel is featured in that an engage hole of a blade body is fitted to an engage projection of a blade body mounting section and a peripheral portion around a lock hole of the blade body is locked in a lock groove of the engage projection.

According to this type of scalpel, however, when detaching the blade body from the blade body mounting section, a user must hold a base end portion of the blade body directly with his one hand and bend it such that the base end portion rises a distance corresponding to the height of the engage projection; this being a troublesome procedure. Further, since the user generally pulls out the blade body while holding its tip portion with the other hand under the condition that the one hand is lifting the base end portion of the blade body, there is a danger of the user's hand getting hurt while the one hand is rubbed by the base end portion of the blade body.

SUMMARY OF THE INVENTION

It is an object of the present invention to provide a cutter which allows a blade body to be lifted for removal without bringing a hand into direct contact with the blade body and thus which assures the easiness of handling and the safety in detaching the blade body.

It is another object of the present invention to provide a cutter which is economical because the cutter becomes again serviceable only by changing a push member when it is fractured.

It is still another object of the present invention to provide a cutter which is configured so that a push member can be easily attached in an accommodating hole.

To achieve the foregoing objects, the present invention provides a cutter composed of a blade body and a stem. The blade body has an engage hole made up of a grip hole and a lock hole which is narrower than the grip hole and is extended to and connected with the grip hole, with a peripheral portion of the lock hole defining a marginal portion. The stem has a blade body mounting section for supporting the blade body being put thereon. The blade body mounting section includes an engage projection adapted to be fitted in the engage hole of the blade body. The engage projection has a lock groove for receiving the marginal portion. The stem is provided with a push member adapted when controlled to push a first portion, on the side of the grip hole, of the blade body, whereby in response to the pushing action of the push member a second portion of the blade body is curved and separated from the engage projection, the second portion being in the vicinity of the grip hole.

Other and further objects of this invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

FIGS. 1 through 6 show a first embodiment of the present invention, in which

FIG. 1 is a perspective view showing a blade-replaceable scalpel in the assembled state;

FIG. 2 is a fragmentary exploded perspective view of the scalpel;

FIG. 3 is a fragmentary sectional view showing a blade body in the course of its being fitted to a blade body mounting section;

FIG. 4 is a fragmentary plan view showing an engage hole of the blade body engaged with an engage projection of the blade body mounting section;

FIG. 5 is a fragmentary sectional view showing the blade body attached to the blade body mounting section; and FIG. 6 is a fragmentary sectional view showing the blade body in the course of its being detached from the blade body mounting section; and FIGS. 7 through 11 show a second embodiment of the present invention, in which FIG. 7 is a fragmentary plan view showing a stem and a blade body mounting section;

FIG. 8 is a fragmentary side view, corresponding to FIG. 7;

FIG. 9 is a fragmentary bottom view, corresponding to FIG. 7;

FIG. 10 is a sectional view taken along line X—X in FIG. 7; and

FIG. 11 is a fragmentary exploded perspective view showing an attaching section and a support plate.

DESCRIPTION OF THE PREFERRED EMBODIMENTS

A first embodiment of the present invention will now be described with reference to FIGS. 1 through 6.

Figure 2:
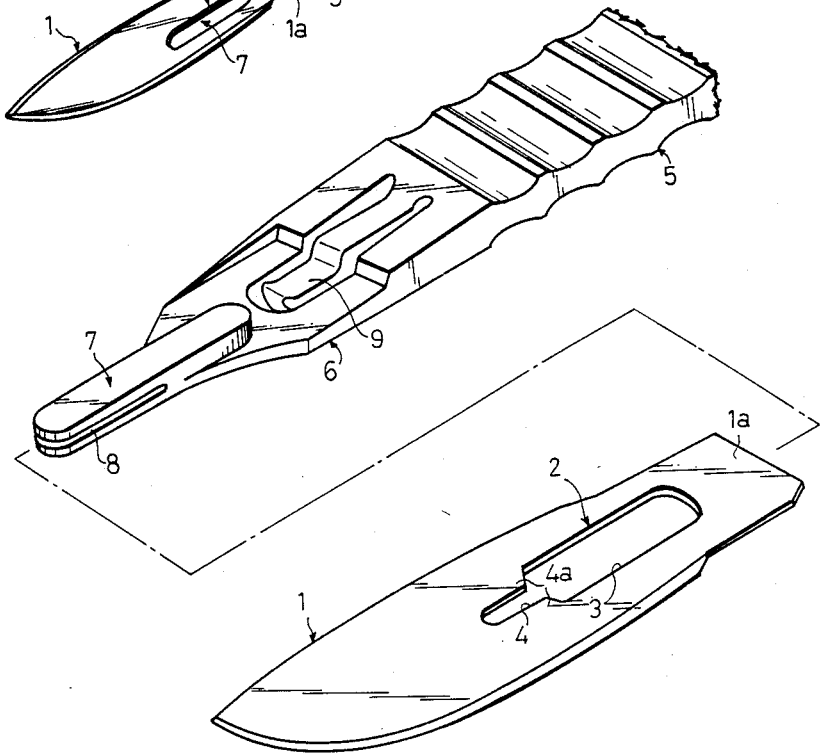

As shown in FIG. 2, a blade body 1 has an elongate engage hole 2 located close to a base end or rear portion 1a thereof. This engage hole 2 is made up of a broad grip hole 3 and a narrow lock hole 4 connected with the tip side or front of the grip hole 3. A stem 5 has a blade body mounting section 6 in a front tip portion thereof on which the blade body 1 is put. The blade body mounting section 6 has an engage projection 7 on one surface thereof to which the engage hole 2 of the blade body 1 is fitted. A tip-side peripheral portion of the engage projection 7 has a U-shaped lock groove 8.

Figure 1:
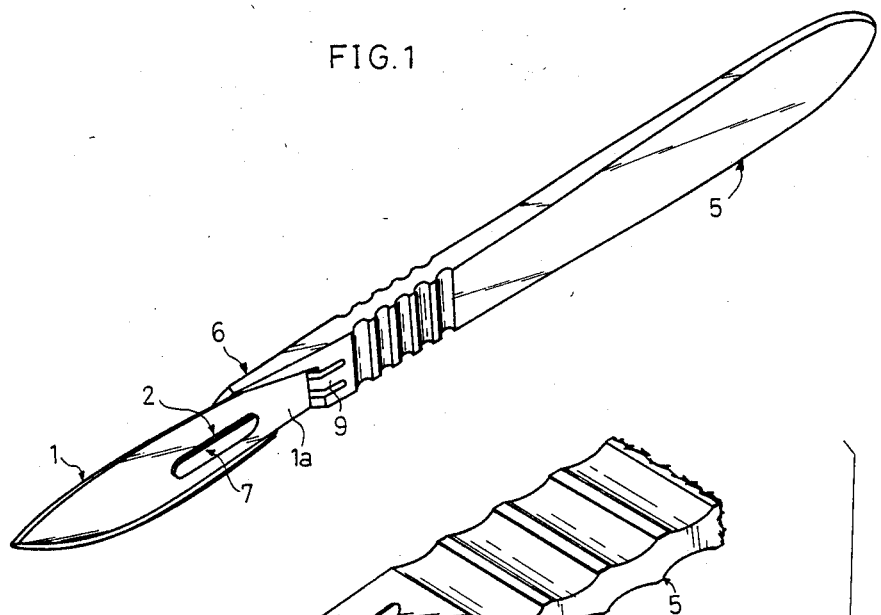
Figure 3:
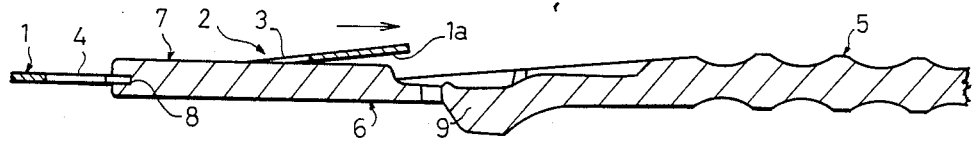
Figure 4:
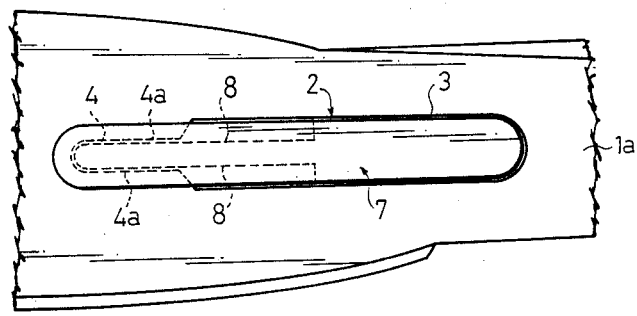
Figure 5:
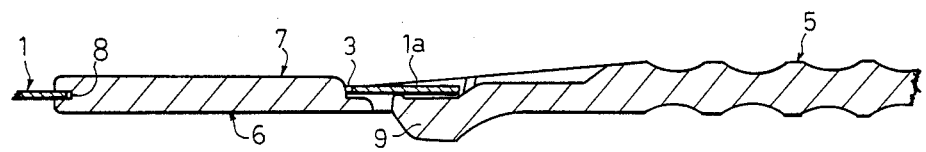

When attaching the blade body 1 to the stem 5, as shown in FIG. 3, put the blade body 1 on the blade body mounting section 6 such that the engage hole 2 of the blade body 1 aligns with the engage projection 7 of the blade body mounting section 6, and then slide the blade body 1 in the direction of the arrow. As a result, as shown in FIGS. 1, 4 and 5, marginal portions 4a on either edge of the lock hole 4 of the blade body 1 are engaged in the lock groove 8 of the engage projection 7 and the engage hole 2 is fitted to the engage projection 7.

Figure 6:
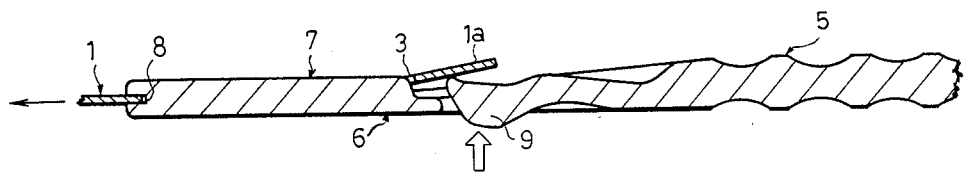

Specifically, in this embodiment, the blade body mounting section 6 has a push section 9 formed integrally, unitarily therewith, serving as a pushing means, which is in the form of a bendable cantilever leaf spring having resiliency, and a tip portion of the push section is located to face the base end portion 1a of the blade body 1. Accordingly, if the push section 9 is pushed with a finger, as shown in FIG. 6, the push section 9 deforms in opposition to its resiliency to push the base end portion 1a of the blade body 1, so that the blade body 1 bends and the base end side of the grip hole 3 disengages from the base end side of the engage projection 7. If the blade body 1 is pulled out in the direction of the arrow while pushing the push section 9, the blade body 1 is detached from the blade body mounting section 6 after passing through the state shown in FIG. 3. If the push section 9 is made free, it returns to the initial state owing to its resiliency.

In this way, the blade body 1 can be detached from the stem 5 by bending the blade body 1, without a need to hold the base end portion 1a of the blade body 1 with fingers. Therefore, the procedure for removing the blade body 1 becomes very easy. In addition, there is no danger of the user's hand getting hurt during handling because no hand touches the base end portion 1a of the blade body 1; thus, the cutter of the present invention is very safe in handling.

Of course, instead of making the push section 9 by the cantilever leaf spring, it may be made of the push button type which includes a coil spring to provide resiliency or of the rotary lever type which has a cam surface for pushing the blade body 1. Further, the stem 5 may be made of metal, synthetic resins, etc. provided that the push section 9 possesses resiliency.

A second embodiment of the present invention will now be described with reference to FIGS. 7 through 11. This embodiment differs from the first embodiment in that the push section is made independent of the stem, so that it is detachable and changeable.

Figure 11:
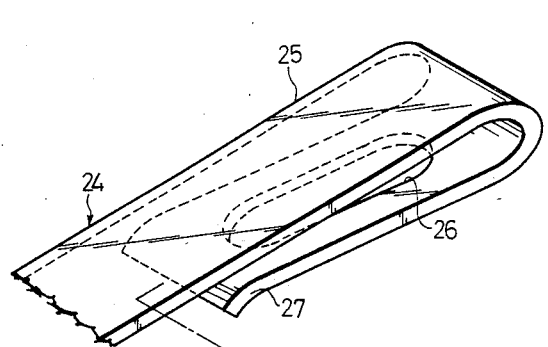
Figure 10:
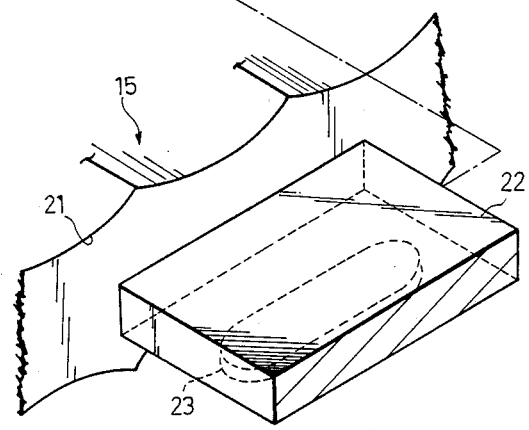
Figure 10:
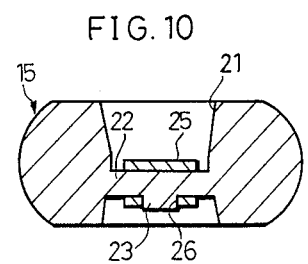

A stem 15 has a blade body mounting section 16 including an engage projection 17 in a tip portion thereof, similarly to the first embodiment, for supporting a blade body 11. The stem 15 has an elongate accommodating hole 21 extending up to the base end of the engage projection 17 in the lengthwise direction of the stem 15. The stem 15 has a flat support plate 22 provided on the base end side of the accommodating hole 21, which plate 22 leaves a certain spacing between it and the base end of the accommodating hole 21. As shown in FIGS. 10 and 11, the support plate 22 has a positioning projection 23 on the under surface thereof which extends in the lengthwise direction of the accommodating hole 21.

Although in this embodiment the stem 15, blade body mounting section 16 and support plate 22 are made integrally by metal, these components may be made independent of one another, and may be made of other than metal.

At a given position inside the accommodating hole 21 there is accommodated and held a push member 24 of the form of a leaf spring, serving as a pushing means. The push member 24 has an attaching section 25 having resiliency in a base end portion thereof. This attaching section 25 has a U-shaped cross section normally as shown in FIG. 11, and is expandable vertically in the drawing. A lower portion of the attaching section 25 has a positioning hole 26 at the position where it aligns with a positioning projection 23 of the support plate 22; this positioning hole 26 being complementary in shape to the positioning projection 23. The distal end of the attaching section 25 is curved downward to define an insertion portion 27. A tip portion of the push member 24 defines a pushing section 28 which is rectangular in cross section.

Figure 7:
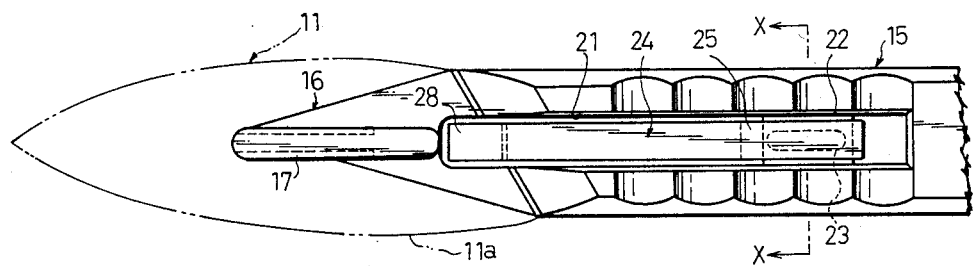
Figure 8:
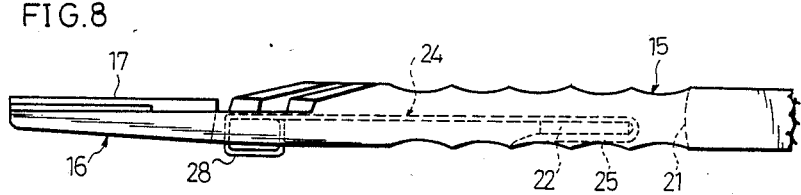
Figure 9:
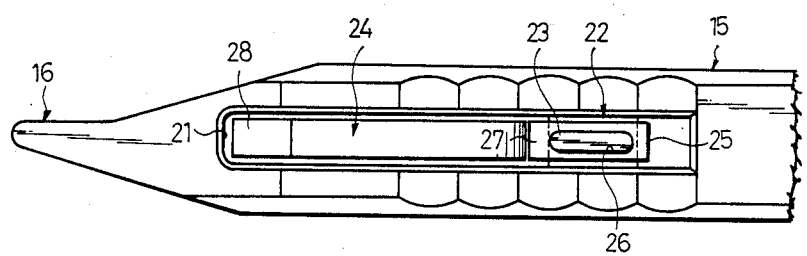

When attaching the push member 24 in the accommodating hole 21, bring the insertion portion 27 into contact with the base end portion of the support plate 22, and then slide the attaching section 25 toward the tip end of the support plate 22. As a result, the attaching section 25 expands vertically in the drawing in opposition to its resiliency and slides along the support plate 22. Then, when the positioning hole 26 of the attaching section 25 comes in alignment with the positioning projection 23 of the support plate 22, the attaching section 25 closes itself owing to its resiliency to pinch the support plate 22, the positioning projection 23 fits in the positioning hole 26 to prevent the movement of the attaching section 25, and the push member 24 is accommodated and held at a given position in the accommodating hole 21. In the thus attained state, as shown in FIGS. 7 and 8, the pushing section 28 of the push member 24 is at the position where it can face a base end portion 11a of the blade body 11 being put in the blade body mounting section 16, and an under portion (see FIG. 8) of the pushing section 28 is exposed a little beyond the under side of the blade body mounting section 16.

The procedure for detaching the blade body 11 from the blade body mounting section 16 and the resulting effects are identical with those of the first embodiment. In addition to the above, this second embodiment makes the push member 24 (serving as a pushing means) independent of the stem 15 and the blade body mounting section 16, thus detachable; accordingly, even when the push member 24 is fractured, it is not necessary to scrap the cutter as a whole, but the cutter becomes again serviceable only by changing the push member 24; thus, the second embodiment is economical. Further, since the push member 24 is configured so that it can be attached in the accommodating hole 21 through the engagement of the attaching section 25 with the support plate 22, the work of attaching the push member is easy.

As many apparently widely different embodiments of this invention may be made without departing from the spirit and scope thereof, it is to be understood that the invention is not limited to the specific embodiments thereof except as defined in the appended claims.

What is claimed is:

1. A cutter, comprising:
   (A) a blade body having lateral sides, said blade body having:
   (i) an engage hole, comprising: a grip hole and a lock hole positioned in front of said grip hole along said blade body, said lock hole being narrower than said grip hole between said lateral sides of said blade body, said lock hole extending to and being connected with said grip hole;
   (ii) a peripheral portion around said lock hole; and
   (iii) a rear portion in the vicinity of said grip hole; and
   (B) a stem positioned generally behind said blade body, said stem having:
   (i) a blade body mounting section for supporting said blade body thereon, said blade body mounting section having an engage projection adapted to be fitted in said engage hole of said blade body, said engage projection having a lock groove defined therein and placed for receiving said peripheral portion of said blade body as said engage projection is moved from said grip hole into said lock hole; and
   (ii) pushing means for pushing said rear portion of said blade body to remove said blade body from said stem, said pushing means comprising a resilient push section which is integral and unitary with said blade body mounting section in the form of a deformable cantilever, said push section having a tip portion adapted to face said rear portion of said blade body to push said rear portion, whereby in response to the pushing action of said pushing means, said blade body is curved and separated from said engage projection.

2. A cutter, comprising:
(A) a blade body having lateral sides, said blade body having:
(i) an engage hole, comprising: a grip hole and a lock hole positioned in front of said grip hole along said blade body, said lock hole being narrower than said grip hole between said lateral sides of said blade body, said lock hole extending to and being connected with said grip hole;
(ii) a peripheral portion around said lock hole; and
(iii) a rear portion in the vicinity of said grip hole; and
(B) a stem positioned generally behind said blade body, said stem having:
(i) a blade body mounting section for supporting said blade body thereon, said blade body mounting section having an engage projection adapted to be fitted in said engage hole of said blade body, said engage projection having a lock groove defined therein and placed for receiving said peripheral portion of said blade body as said engage projection is moved from said grip hole into said lock hole; and
(ii) pushing means for pushing said rear portion of said blade body to remove said blade body from said stem;
said pushing means comprising a push member detachably attached to said stem, said push member having a pushing section adapted to face said rear portion of said blade body and to push said rear portion;
said push member being in the form of a leaf spring having one end which has said pushing section and having an attaching section adapted to be detachably attached to said stem;
said stem having an accommodating hole for accommodating said push member; and
said stem further including a support plate provided in said accommodating hole for supporting said attaching section, and said attaching section of said push member having resiliency and being substantially U-shaped so that it pinches said support plate from both sides in the thickness direction;
whereby in response to the pushing action of said pushing means, said blade body is curved and separated from said engage projection.

3. A cutter according to claim 2, wherein said attaching section has a positioning hole, and said support plate has, in a portion facing said positioning hole in the thicknesswise direction, on one surface thereof, a positioning projection adapted to be fitted in said positioning hole for positioning said push member in said accommodating hole.

* * * * *